US007654825B2

United States Patent
Ray

(10) Patent No.: US 7,654,825 B2
(45) Date of Patent: Feb. 2, 2010

(54) DENTAL VIBRATOR AND ACOUSTICAL UNIT WITH METHOD FOR THE INHIBITION OF OPERATIVE PAIN

(76) Inventor: Charles D. Ray, 4320 Via Presada, Santa Barbara, CA (US) 93110

( * ) Notice: Subject to any disclaimer, the term of this patent is extended or adjusted under 35 U.S.C. 154(b) by 141 days.

(21) Appl. No.: 11/144,448

(22) Filed: Jun. 3, 2005

(65) Prior Publication Data

US 2006/0275739 A1     Dec. 7, 2006

(51) Int. Cl.
*A61C 5/00* (2006.01)
(52) U.S. Cl. ............... 433/215; 433/138; 433/139; 433/229
(58) Field of Classification Search ........... 433/215, 433/138, 139, 229; 128/867; 607/46, 47
See application file for complete search history.

(56) References Cited

U.S. PATENT DOCUMENTS

| | | | | |
|---|---|---|---|---|
| 3,908,634 | A * | 9/1975 | Monaghan | 600/28 |
| 4,924,880 | A * | 5/1990 | O'Neill et al. | 607/47 |
| 5,437,606 | A * | 8/1995 | Tsukamoto | 601/2 |
| 5,496,256 | A * | 3/1996 | Bock et al. | 601/2 |
| 5,518,008 | A * | 5/1996 | Cucchiaro et al. | 600/590 |
| 5,622,496 | A * | 4/1997 | Champagne | 433/39 |
| 5,647,851 | A * | 7/1997 | Pokras | 604/131 |
| 5,980,528 | A * | 11/1999 | Salys | 606/99 |
| 6,115,477 | A * | 9/2000 | Filo et al. | 381/151 |
| 6,226,510 | B1 * | 5/2001 | Boling et al. | 455/404.2 |
| 6,293,796 | B1 * | 9/2001 | Trom et al. | 433/155 |
| 2003/0172939 | A1 * | 9/2003 | Hirchenbain et al. | 128/867 |
| 2005/0032017 | A1 * | 2/2005 | Levy | 433/29 |

OTHER PUBLICATIONS

Gray, Henry. Anatomy of the Human Body. Philadelphia: Lea & Febiger, 1918; Bartleby.com, 2000. www.bartleby.com/107/. Chapter IX, Section 5e, [Apr. 22, 2009].*

* cited by examiner

*Primary Examiner*—Cris L Rodriguez
*Assistant Examiner*—Michael R Ballinger
(74) *Attorney, Agent, or Firm*—Dicke, Billig & Czaja, PLLC

(57) ABSTRACT

A patient-controlled device for inhibiting intraoperative dental pain is disclosed. The device includes a removable tooth clamp, an actuator unit, and a control box. The actuator defines unit includes a vibratory actuator and a coupling device for coupling the vibratory actuator to the tooth clamp. The control box is electrically connected to the vibratory actuator and includes at least one controller. In this regard, the removable tooth clamp is configured to be attached to at least one tooth of a patient, and upon final assembly, the controller initiates oscillation of the tooth clamp via the vibratory actuator and vibrates the tooth/teeth to inhibit intraoperative dental pain.

8 Claims, 1 Drawing Sheet

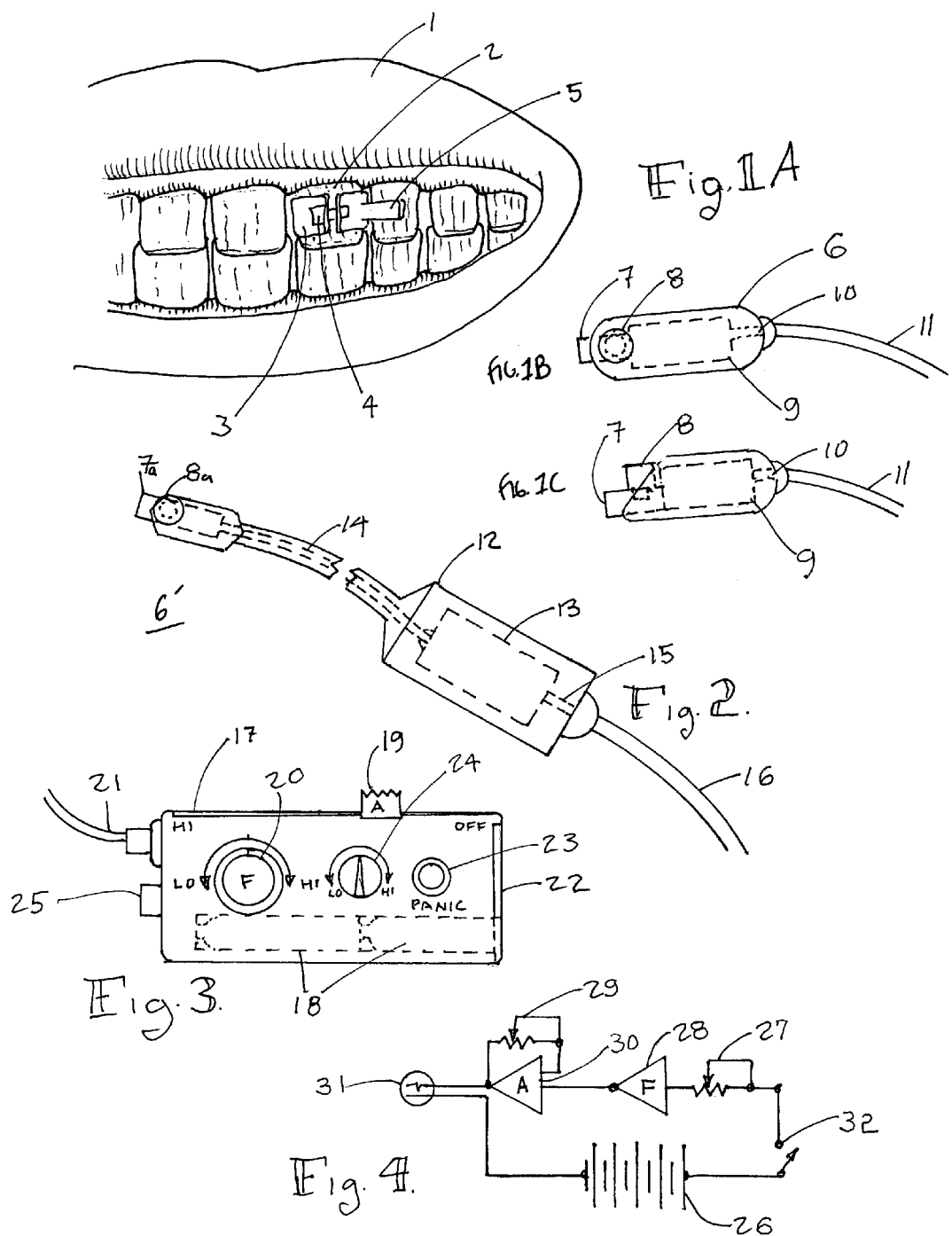

DENTAL VIBRATOR AND ACOUSTICAL UNIT WITH METHOD FOR THE INHIBITION OF OPERATIVE PAIN

FIELD OF THE INVENTION

Aspects of the present invention relate to an inhibition of intraoperative dental pain, and more particularly, to a patient-controlled device for inhibiting intraoperative dental pain.

BACKGROUND

In 1965 neurophysiologists Ronald Melzack and Patrick Wall described what became known as the 'Gate Theory' of sensation, principally painful sensation. (Melzack R, Wall P D: Pain mechanisms: A new theory. Science 150:971,1965.) Basically they showed that input signals from painful stimuli, on reaching the spinal nerves, via normal connecting nerve fibers, were subjected to an anatomical 'gate' or switch in a specific part of the spinal cord. This gate, by incoming signal type and intensity, determined if the signals would be passed up the spinal cord to the sensory areas of the brain or locally blocked. Painful stimuli of sufficient intensity and arising from specific areas from peripheral injuries are passed by this 'gate' if unopposed by other sensory input; this mechanism alerts the patient to potential or actual tissue injury. These investigators proved that non-painful stimuli of sufficient amplitude and from similar locations as the pain source could 'close' the 'gate' to the painful signals, blocking their transmission upward to conscious experience. It was shown in experiments and later in very large clinical application that electrical 'tingling' stimuli could inhibit the experience of pain. On this concept a substantial industry was built using electrical stimulation for pain control. Further, the gate theory showed that other non-painful stimulus, such as vibration or distraction through massage or the application of liniment, heat or cold to the overlying skin in many parts of the body including the face and head, could likewise inhibit the sensation of pain in the same areas. Distant distraction of pain is also well known. For example, the ancient practice of 'biting on a bullet' or clenching objects during childbirth is related to such inhibition by a conflicting sensory input although at a different location in the central nervous system. Additionally, acupuncture may provide the distracting sensation that can reduce pain perception. These phenomena had long been known but the scientific proof and understanding had been lacking until the work by Melzack and Wall and many subsequent investigators.

For dental pain suppression, pulsatile electrical stimulation of gums, tongue or roof of the mouth is potentially useful but not practical due to the easy dislodgment of the electrodes which might otherwise unfortunately need to be firmly attached, perhaps by sewing to the tissues or cyanoacrylate gluing to the surfaces of these structures. Further should the location of stimulation might need changing during the procedure, it would be difficult if using tissue-attached electrical stimulator electrodes. Teeth are supplied with pain fibers that also weakly detect temperature and pressure changes; however, gums and adjacent soft tissues are sensitive to electrical stimulation, touch and vibration.

One known approach to inhibit periodontal pain is practiced in a simple but limited form by dentists when they rapidly and intermittently tug gently on teeth or lips near the site of a needle puncture during, for example, infiltration of local anesthesia into and through the gums. This tugging distracts the sensation of immediate pain of the needle stick and passing of the needle through the gum, aiming at the dental nerve at its entrance to the root of the tooth or teeth. Other methods of distraction are also employed such as music or white noise provided through patient earphones or even electrical stimulation of the face. A local surface anesthetic material may be applied to the gum before the needle enters but this does not help for deeper passage of the needle or during the surgical procedure.

With the above Background in mind, improvements to, and advancement of, pain suppression during dental surgery will be welcomed by both dental caregivers and by patients.

SUMMARY

One aspect of the present invention provides a patient-controlled device for inhibiting intraoperative dental pain. The device includes a removable tooth clamp an actuator unit, and a control box. The actuator unit includes a vibratory actuator and a coupling device for coupling the vibratory actuator to the tooth clamp. The control box is electrically connected to the vibratory actuator and includes at least one controller. In this regard, the removable tooth clamp is configured to be attached to at least one tooth of a patient, and upon final assembly, the controller initiates oscillation of the tooth clamp via the vibratory actuator and vibrates the at least one tooth to inhibit intraoperative dental pain.

Another aspect of the present invention provides a method of inhibiting intraoperative dental pain. The method includes providing a patient with a control box including at least one controller. The method additionally includes removably attaching a tooth clamp to at least one tooth of the patient, the tooth clamp including a prong. The method further includes connecting a prong receptor of an actuator unit to the prong, the actuator unit including a vibratory actuator. The method further includes electrically connecting vibrating actuator to the control box, and energizing the vibrating actuator. In this regard, patient-controlled movement of the controller translates to a vibratory movement of the tooth/teeth of the patient to inhibit a sensation of pain.

Aspects of the novel tooth vibrator unit include a solid state piezoelectric device made of, for example, platinum-barium titanate ceramic, or a pulse controlled magnetic coil with high Oersted core material such as a ferrite which vibrates vigorously at a controlled amplitude and frequency as controlled by a power source remotely operated. In this regard, the term piezoelectric includes any device that translates/converts an electrical signal, pulse, or current to a mechanical movement or vibration. The active vibratory unit is attached to selected anterior or posterior surfaces of one or more adjacent teeth using, in one embodiment, standard flat metal bands with screw tightening mechanism as now applied in restorative dentistry to contain the placement of a semi-fluidic, self-hardening material. The band of thin, flat metal is gently forced around a selected tooth or between and around adjacent teeth and tightened. A small fixation means, for example a prong of flexible metal, suitably attached on this flat band is then used to removably attach the vibratory transducer as here disclosed or employing a similar means. Initially, the dentist activates the mechanism and determines the level of comfort for the patient receiving the vibratory sensation. The cooperative patient is then given a wired controller to hold by hand and on instruction makes a series of suggested trial adjustments, higher and lower in amplitude and higher and lower in pulse frequency to become acquainted with the variable sensations and the use of the controller. The patient is also shown the presence of the 'panic' button that can be used if the method were to completely fail to control pain, so signaling the dentist. If the patient is also to wear earphones for the supply of music or white noise, that volume control is also located on the same wired controller. All of the parameter adjusting knobs are individually formed to be easily discriminated by tactile finger contact so that the patient does not need to directly view the control knobs. The dentist also reminds the patient that the patient himself is in control of the stimulation and the sound and at no time will these interfere with the dentist's surgical procedure, or if the vibration or sound are not sufficiently effective their use can be augmented through applying a variety of methods and medications including a return to anesthetic infiltration of the nerves to the teeth or other medications or means.

BRIEF DESCRIPTION OF THE DRAWINGS

Embodiments of the invention are better understood with reference to the following drawings. The elements of the drawings are not necessarily to scale relative to each other. Like reference numerals designate corresponding similar parts.

FIG. 1A is a diagrammatic frontal plan view of the open mouth showing a clamp means applied to an upper left incisor tooth in accordance with the present invention. The novel device can be adapted to mount on any tooth or a plurality of teeth utilizing adapted, dental attachment means (i.e., an adapted dental implement fixed to a tooth/teeth). Permanently affixed to the attachment means is a mounting prong onto which the tooth vibrator means will be firmly and removably attached. Additional views of FIGS. 1B and 1C show the actuator (i.e., vibrator unit) in accordance with the present invention in both a frontal and in a lateral view having a receptor means to clip on or attach to the tooth prong of FIG. 1A.

FIG. 2 is a diagrammatic elevation, showing a remote actuator in accordance with the present invention in conjunction with a means of attachment to the tooth attachment prong. In this regard, in one embodiment the actuator is a piezoelectric or electromechanical actuator. During use, vibratory force is transmitted by a flexible core wire from the actuator to the tooth prong, providing greater vibratory power from a more remote location, if needed by the dentist.

FIG. 3 is a diagrammatic view of a control box in accordance with the present invention, useful with the actuators of FIGS. 1A-1C and 2, and including a power unit. Control dials operated by the patient vary the intensity and frequency of the vibration transmitted to the tooth or teeth to which the actuator is directly (or indirectly) attached. In one embodiment, a separate control dial is provided to adjust a volume of an audio signal. The controls for each parameter are easily determined by the patient after a short practice period. The battery compartment is shown. The simple electrical circuit is mounted on a standard printed circuit board and suitably mounted within the power unit. The power cable connection at the end of the power unit is shown.

FIG. 4 is a diagram of a representative battery operated electrical circuit providing controllable vibratory amplitude and frequency variation under control by the patient. The amplitude slider control also switches off the power in its most minimal position. For one skilled in the art, other circuit designs may be substituted without changing the intent and performance of the invention.

DETAILED DESCRIPTION

In the following Detailed Description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

FIGS. 1A 2 illustrate diagrammatically embodiments of the invention where vibratory sensory stimulation is applied producing dental procedural pain interference. In general terms, the intraoperative dental pain control device of the present invention includes a dental clamping device, a vibratory actuator, and a control device. The dental clamping device physically couples the actuator to a tooth or teeth of the patient, whereas the control device facilitates control of energy delivered to/by the actuator. In the following discussion, ceramic piezoelectric and induction-wound electromechanical actuator vibrators are indicated, but those with skill in the electromechanical arts will recognize that other actuators could be similarly employed. In this regard, appropriate actuators will respond to the driving electrical energy at the desired spectrum of frequencies and amplitudes.

With reference to FIG. 1, between the lips 1 of the patient's open mouth, chosen teeth 2 are shown and to which a dental clamping means 3 is removably attached and made firm by a fastening means 4. In this regard, the dental clamping means 3 can include mechanical rings, opposed metal bands, and other dental implements configured to removably fasten to and stabilize one or more teeth of a patient. To this stabilized clamping means 3, a permanent prong 5 is bonded to which subsequent vibratory means will be removably fixed.

Illustrated in a planar view (FIG. 1B) and in a side view (FIG. 1C) is a self-contained vibratory actuator unit 6 having coupling means 7 for attachment to the prong 5 (FIG. 1A). Coupling means 7, in one embodiment, includes structure 8 adapted for selective attachment to the prong 5 (e.g., the structure 8 can by a tube or cylinder sized to frictionally mount over the prong 5). The actuator unit 6 is supplied with power through wires 10 formed within a power cable 11. In one embodiment, the actuator 6 includes a ceramic piezoelectric actuator 9 electrically connected to the cable 11 and mechanically connected to the coupling means 7. Alternatively, other actuator materials can be employed. Even further, and as described below, the actuator material can be located remote of the coupling means 7. Regardless, the actuator unit 6 is adapted to apply vibratory energy to the prong 5 via the coupling means 7.

FIG. 2 illustrates an alternative embodiment remote actuator unit 6' having greater power than the actuator 6 illustrated in FIGS. 1B and 1C. The actuator unit 6' has a similar attachment means 7a and fixing means 8a to firmly but removably attach the actuator 6' to the prong 5, as disclosed above. In addition, the actuator 6' includes a contained unit 12 that houses a piezoelectric or induction magnetic actuator 13, which through a suitably stiff yet flexible wire or rod-like core 14 of a connector cable transmits vibratory motion to the prong 5 (FIG. 1A) upon final assembly. The actuator unit 6' has a power cable 16 with terminal fittings matching those of the power cables 11 as depicted in FIGS. 1B and 1C.

FIG. 3 illustrates one embodiment of a patient hand held power or control box 17 in accordance with the present invention having a suitable battery compartment 18, and one or more controllers such as a sliding control 19 for amplitude (A) and a dial 20 for frequency (F) of the power delivered to the actuator unit (such as the actuator units 6, 6' of FIGS. 1B and 2). The above-disclosed cables 11 (FIG. 1B) and 16 (FIG. 2) have suitable means to removably connect to the power unit 17 at a plug terminal 21. The battery compartment 18 is preferably waterproof and has an access door 22 (shown schematically). In case of insufficiently controlled pain or other patient concern, the patient (not shown) can communicate with the dentist by pressing a "panic" button 23 on the control power unit 17. In one embodiment, the panic button 23 actuates one or both of a buzzer and flashing LED light inside the power unit. An audio volume control 24 can be provided that controls adjustment of the loudness for the patient-worn earphones (not shown) that can be connected into a jack 25 on the control power unit 17. An audio FM receiver and audio amplifier (not shown) can be provided inside the control power unit 17 that are switched on by the volume control 24. The entire control power unit 17 can be suitably cleansed and sanitized using, for example, a water-soluble liquid disinfection medium. The positions of the controls are easily determined by tactile feel by the patient so he does not need to look at the controls to determine their positions. The sliding amplitude control 19 can be adjusted from maximum (HI) to OFF as indicated. The frequency control 20 rotates from HI clockwise to LO counterclockwise, as is standard for rotary controls. Alternatively, the controls 19, 20, 23, and 24 can assume a variety of other forms. Further, one or more of the controls 19, 20, 23, and 24 can be eliminated and/or other controls added.

FIG. 4 illustrates one embodiment of a battery-operated electrical circuit having signal conditioning amplifiers A for amplitude and F for frequency adjustment. Batteries 26 supply current to a frequency amplitude control 27 then through amplifier F 28 and then through amplitude control 29 to amplifier A 30 to a plug connector 31 to which cables 11 (FIG. 1B) or 16 (FIG. 2) may be removably attached. The amplitude slider 29 also operates a power off switch 32 in its most minimal amplitude setting OFF 19 on the power unit 17 of FIG. 3.

Relative to the control unit 17 of FIG. 3, not illustrated in FIG. 4 are the simple battery operated panic buzzer and indicator LED to notify the dentist in case of pain or other pressing need. Further, not illustrated is the source of the music or white noise as wirelessly transmitted from a nearby FM transmitter unit and received by the suitable small circuit inside the present power control unit. Components of such a system are obtainable from a radio supply source.

Method and Example of Use

With reference to FIGS. 1-3, A thin metal removable tooth clamp 3 is passed around the tooth 2 or teeth adjacent to or near the one to be injected with anesthetic or those to be operated upon. The removable tooth clamp 3 is, in one embodiment, similar to clamps used by dentists to surround a tooth for the containment of a semi-fluid, self hardening material employed in dental repair or reconstruction. The band or clamp 3 is suitable tightened, for example, via a screw mechanism 4. Permanently fixed to the band 3 is a prong 5, to which the vibratory actuator-transducer unit 6 or 6' is removably attached, and positioned so that it does not interfere with the dental procedure to be performed. Should it be found to physically interfere, the band 3 can be moved to a more suitable location or placed on other teeth, so long as it is located in the same nerve supply zone as the area to be injected or operated upon. The vibratory transducer unit 6 or 6', whether of a ceramic or inductive electrical coil type, is removably attached to the prong 5, or through an extension mechanical cable connected to the remotely placed transducer/vibrator. In giving the patient a series of training demonstrations the dentist teaches the patient how to adjust typical preferred settings for use of the stimulator and audio components.

The hand-held control unit 17 provides the electrical control signals to the transducer and, in one embodiment, audio signals to the earphones (not shown). This control unit 17 is held and operated by the patient (not shown) and adjusted as needed to mask the pain of the procedure. The hand held unit 17 is used to adjust the amplitude or strength of the vibration and separately the frequency, as well as the volume of the audio signals in one embodiment. Further, in one embodiment, there is a panic button 23 on the unit 17 that alerts the dentist if the vibratory and/or audio means are insufficient to the control of pain. Through the earphones, either music or white noise is presented to the patient, the volume being controlled by an appropriate knob on the power control unit 17. The operating controls, knobs, slides and the like, on the control unit are tactile-evident to the patient so that he does not need to move his head or eyes to look for or adjust the appropriate control.

The dentist gives the patient one or more trial demonstrations after which the patient makes adjustments of each parameter as desired or needed during further learning trials and clearly during the actual operative procedure.

Advantages

The invention has the novel ability to obtain sufficient analgesic masking of operative dental pain using a non-chemical, non-narcotic, benign, instantly adjustable and interruptible, non-addicting, simple mechanically driven means. The method is extremely safe, and under control by the patient at all times. The device and method can be used with or without adjunctive medication, locally or systemically applied as required by the particular patient. The patient to whom the novel device is applied utilizes a simple hand-held control unit that permits continuous adjustment of the distracting vibratory or acoustic stimuli as desired. Short training sessions are given the patient by the dentist prior to beginning the dental procedure thus acquainting the patient with the distracting sensations and his overriding control of them. No part of the system presents an obstruction to the proper performance of the planned dental procedure.

While the preferred embodiments of the invention have been described, it should be understood that various changes, adaptations and modifications may be made therein by those skilled in the art without departing from the spirit of the invention and the scope of the appended claims.

The device described above, in many cases, obviates a need for infiltration of, or intravenous or inhaled, anesthetic drug delivery during a dental surgical procedure. The device does not produce discomfort in its application and use and indeed may be comforting to the patient, even though a different sensation of tingling, tickling, music and/or noise is perceived.

The application of completely benign vibration to teeth is devoid of any undesirable side effect such as allergic reaction to a topical anesthetic or rare but potentially deadly anaphylaxis to the local infiltrated medication. The sensory interference effect is immediate and continuous. With the device disclosed herein, the patient using a hand-held controller, advantageously adding to his distraction by participation in the method, can adjust the amplitude and waveform of the vibration. During 'rest' periods of the surgery when potential pain is low, the patient can turn down or off the inhibitory sensations. When the procedure is finished, the patient turns the unit off and has no residual effects such as the bothersome injected, post-anesthetic numbness and sagging of the face that normally lasts for a few hours.

The vibrating transducer can be constructed and attached to a tooth or teeth in a variety of ways. Preferred means to deliver the vibration to teeth can an extension of a vibrating flex cable, a pulsating hydraulic pressure transmitted via an attached tube, or a vibratory solid state transducer suitably clamped to the tooth or teeth selected. The latter method is disclosed here although persons skilled in the mechanical arts can adapt the concept to a variety of means to cause desirable distracting vibration to be applied to the tooth or teeth. No other vibratory device or method serving this application or in combination with an acoustical stimulus all under patient control is known to exist at this time.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method of inhibiting intraoperative dental pain during a dental procedure comprising:
   providing a patient with a control box;
   locating a nerve supply zone of a tooth to be operated upon;
   identifying at least one tooth in the nerve supply zone apart from the tooth to be operated upon;
   removably attaching a tooth clamp to the identified at least one tooth, the tooth clamp including a prong;
   connecting a prong receptor of an actuator unit to the prong, the actuator unit including a vibratory actuator;
   electrically connecting actuator unit to the control box; and
   energizing the vibratory actuator to vibrate the identified at least one tooth to inhibit a sensation of pain;
   wherein the method is characterized by a tooth clamp not being directly attached to the tooth to be operated upon.

2. The method of claim 1, wherein the method is characterized by the absence of providing the patient with anesthesia.

3. The method of claim 1, wherein the control box includes a controller, the method further comprising:
   manipulating the controller by the patient to adjust the amount of vibrating energy delivered to the patient's tooth.

4. The method of claim 1, further comprising:
   performing a dental procedure on the patient while the vibratory actuator is energized, the dental procedure being different from the energizing of the vibratory actuator.

5. The method of claim 1, wherein the method is characterized by the vibratory actuator remaining outside of a mouth of the patient.

6. The method of claim 1, wherein removably attaching a tooth clamp includes:
   a) providing the tooth clamp to include a band and a screw mechanism;
   b) placing the band around the identified at least one tooth; and
   c) operating the screw mechanism to firmly tighten the band to the identified at least one tooth;
   wherein the screw mechanism independently maintains the tightened band.

7. The method of claim 6, wherein the band and the screw mechanism combine to define a closed loop, and further wherein placing the band around the identified at least one tooth includes the loop having a first size, and even further wherein operating the screw mechanism includes the screw mechanism transitioning the loop to a second size, the second size being smaller than the first size.

8. A method of inhibiting intraoperative dental pain comprising:
   providing a patient with a control box;
   locating a nerve supply zone of a tooth to be operated upon;
   identifying at least one tooth in the nerve supply zone apart from the tooth to be operated upon;
   removably attaching a tooth clamp to the identified at least one tooth, the tooth clamp including:
   a) providing the tooth clamp to include a band and a screw mechanism;
   b) placing the band around the identified at least one tooth; and
   c) operating the screw mechanism to firmly tighten the band to the identified at least one tooth;
   connecting a prong receptor of an actuator unit to the prong, the actuator unit including a vibratory actuator;
   electrically connecting actuator unit to the control box; and
   energizing the vibratory actuator to vibrate the identified at least one tooth to inhibit a sensation of pain;
   wherein the screw mechanism independently maintains the tightened band.

* * * * *